US010106334B2

(12) United States Patent
Yamazaki et al.

(10) Patent No.: US 10,106,334 B2
(45) Date of Patent: Oct. 23, 2018

(54) MEASUREMENT APPARATUS, MEASUREMENT METHOD, AND CORRECTION METHOD

(71) Applicant: Lasertec Corporation, Yokohama (JP)

(72) Inventors: Teruaki Yamazaki, Yokohama (JP); Hiroyuki Jitsukawa, Yokohama (JP)

(73) Assignee: Lasertec Corporation, Yokohama (JP)

( * ) Notice: Subject to any disclaimer, the term of this patent is extended or adjusted under 35 U.S.C. 154(b) by 0 days.

(21) Appl. No.: 15/620,333

(22) Filed: Jun. 12, 2017

(65) Prior Publication Data

US 2017/0355532 A1    Dec. 14, 2017

(30) Foreign Application Priority Data

Jun. 13, 2016    (JP) ................................ 2016-117011

(51) Int. Cl.

| | | |
|---|---|---|
| *G01N 21/00* | (2006.01) | |
| *B65G 47/24* | (2006.01) | |
| *G01B 11/24* | (2006.01) | |
| *G01B 11/00* | (2006.01) | |

(52) U.S. Cl.
CPC .............. *B65G 47/24* (2013.01); *G01B 11/00* (2013.01); *G01B 11/2408* (2013.01); *G01N 21/00* (2013.01)

(58) Field of Classification Search
CPC ........... G01N 21/9501; G01N 21/9503; G01N 21/8806; G01N 21/94; G01N 21/956; G01N 2201/06113; G01N 21/88; G01N 21/8851; G01N 21/95; G01N 21/952; G01N 21/47;

(Continued)

(56) References Cited

U.S. PATENT DOCUMENTS

| | | | |
|---|---|---|---|
| 2005/0036671 A1* | 2/2005 | Watkins | ............. G01N 21/9503 382/145 |
| 2009/0130784 A1 | 5/2009 | Michelsson et al. | |
| 2013/0100441 A1* | 4/2013 | Tagawa | ............. G01N 21/9503 356/237.5 |

FOREIGN PATENT DOCUMENTS

| | | |
|---|---|---|
| JP | H1123219 A | 1/1999 |
| JP | 2000074622 A | 3/2000 |
| JP | 2000294608 A | 10/2000 |

(Continued)

OTHER PUBLICATIONS

Japan Patent Office, Office Action Issued in Application No. 2016-117011, dated Jun. 27, 2017, 9 pages.

(Continued)

*Primary Examiner* — Michael P Stafira
(74) *Attorney, Agent, or Firm* — McCoy Russell LLP (57) ABSTRACT

A measurement apparatus 1 according to the present invention includes a table 10 that has an axis of rotation 14 and supports a disc-shaped object 40, a first driving unit that rotates the table 10 around the axis of rotation 14, a light source 50 that produces illumination light with which an end portion 45 of the disc-shaped object 40 is illuminated, an objective lens 60 that collects the illumination light reflected from the end portion 45, a second driving unit that moves the objective lens 60 along an optical axis 64, an imaging unit 70 that captures an image of the end portion 45 by detecting the reflected light collected by the objective lens 60, and an autofocus optical system 80 that determines a position of the objective lens 60 where the image of the end portion 45 is brought into focus in the imaging unit 70.

12 Claims, 5 Drawing Sheets

(58) Field of Classification Search
CPC .......... G01N 21/909; G01N 21/95607; G01N 2201/12
See application file for complete search history.

(56) References Cited

FOREIGN PATENT DOCUMENTS

| | | | |
|---|---|---|---|
| JP | 2002151575 | A | 5/2002 |
| JP | 2003207323 | A | 7/2003 |
| JP | 2003256811 | A | 9/2003 |
| JP | 2004325389 | A | 11/2004 |
| JP | 2006201360 | A | 8/2006 |
| JP | 2007206441 | A | 8/2007 |
| JP | 2009085766 | A | 4/2009 |
| JP | 2009121911 | A | 6/2009 |
| JP | 2012117871 | A | 6/2012 |
| JP | 2013171042 | A | 9/2013 |
| JP | 2014109480 | A | 6/2014 |
| JP | 2014167462 | A | 9/2014 |
| JP | 2016045117 | A | 4/2016 |

OTHER PUBLICATIONS

Japan Patent Office, Office Action Issued in Application No. 2016-117011, dated Aug. 1, 2017, 8 pages.

\* cited by examiner

MEASUREMENT APPARATUS, MEASUREMENT METHOD, AND CORRECTION METHOD

INCORPORATION BY REFERENCE

This application is based upon and claims the benefit of priority from Japanese patent application No. 2016-117011, filed on Jun. 13, 2016, the disclosure of which is incorporated herein in its entirety by reference.

BACKGROUND

The present invention relates to a measurement apparatus, a measurement method, and a correction method, and particularly to a measurement apparatus and a measurement method for measuring the amount of eccentricity at the time when a wafer is rotated on a table and to a correction method.

In an apparatus in which a disc-shaped object, for example, a wafer is sucked on a table and rotated around the axis of rotation of the table, it is necessary to accurately measure the amount of eccentricity of the wafer for scanning the wafer around the axis of rotation.

For example, Japanese Unexamined Patent Application Publication Nos. 2006-201360, 2013-171042, 2009-121911, 2009-085766, 2000-294608, 2007-206441, and 2016-045117 each disclose an apparatus that images the end portion of a wafer rotated on a table.

The methods disclosed in Japanese Unexamined Patent Application Publication Nos. 2006-201360, 2013-171042, 2009-121911, 2009-085766, and 2000-294608 each include determining the shape of the wafer by observing the end portion of the wafer and therefore requires time for the determination of the shape of the wafer or requires a large number of components, such as a plurality of light sources.

The methods disclosed in Japanese Unexamined Patent Application Publication Nos. 2007-206441 and 2016-045117 each include translating the wafer in accordance with an error in circularity of the wafer or an error in position where the wafer is placed, for focusing error control. Since the amount of eccentricity is not correlated with the position along the end portion, the accuracy in the measurement of the amount of eccentricity cannot therefore be improved.

The methods disclosed in the related art therefore have difficulty in measuring the amount of eccentricity of a disc-shaped object supported by a rotating table with accuracy at low cost.

The present invention has been made to solve the problems described above, and an object of the present invention is to provide a measurement apparatus and a measurement method for measuring the amount of eccentricity of a disc-shaped object supported by a rotating table with accuracy at low cost and further provide a correction method.

SUMMARY

A measurement apparatus according to the present invention includes a table that has an axis of rotation and supports a disc-shaped object, a first driving unit that rotates the table around the axis of rotation, a light source that produces illumination light with which an end portion of the disc-shaped object is illuminated, an objective lens that collects the illumination light reflected from the end portion, a second driving unit that moves the objective lens along an optical axis of the objective lens, an imaging unit that captures an image of the end portion by detecting the reflected light collected by the objective lens, an autofocus optical system that determines a position of the objective lens along the optical axis where the image is brought into focus in the imaging unit, and a control unit that controls the first driving unit and the second driving unit, and the control unit moves the objective lens to the position determined by the autofocus optical system and adds predetermined additional data to data on the image. According to the configuration described above, the amount of eccentricity of the disc-shaped object can be measured with accuracy at low cost.

The additional data may be a position of the end portion and a position of the objective lens along the optical axis at the time when the image is captured. According to the configuration described above, the amount of eccentricity can be correlated with the position of the end portion.

The imaging unit may include a plurality of pixels arranged in one direction, and the plurality of pixels may image the end portion along the axis of rotation. According to the configuration described above, the amount of eccentricity of the disc-shaped object can be measured with accuracy.

The control unit may calculate an amount of eccentricity between the axis of rotation and the center of the disc-shaped object based on positions of the objective lens along the optical axis that are obtained by one turn of the disc-shaped object. According to the configuration described above, the amount of eccentricity can be measured at low cost.

The measurement apparatus may further includes a third driving unit that moves the table, and the control unit may move the table based on the amount of eccentricity. According to the configuration described above, the amount of eccentricity can be corrected with accuracy.

A measurement method according to the present invention includes placing a disc-shaped object on a table having an axis of rotation, rotating the table around the axis of rotation, illuminating an end portion of the disc-shaped object with illumination light, collecting the illumination light reflected from the end portion with an objective lens, capturing an image of the end portion by detecting the reflected light collected by the objective lens, determining a position of the objective lens along the optical axis where the image is brought into focus by using an autofocus optical system, moving the objective lens to the position determined by the autofocus optical system, and adding predetermined additional data to data on the image. According to the configuration described above, the amount of eccentricity of the disc-shaped object can be measured with accuracy at low cost.

The additional data may be a position of the end portion and a position of the objective lens along the optical axis at the time when the image is captured. According to the configuration described above, the amount of eccentricity can be correlated with the position of the end portion.

A plurality of pixels arranged in one direction may image the end portion along the axis of rotation. According to the configuration described above, the amount of eccentricity of the disc-shaped object can be measured with accuracy.

An amount of eccentricity between the axis of rotation and the center of the disc-shaped object may be calculated based on positions of the objective lens along the optical axis that are obtained by one turn of the disc-shaped object. According to the configuration described above, the amount of eccentricity can be measured at low cost.

A correction method according to the present invention includes placing a disc-shaped object on a table having an axis of rotation, rotating the table around the axis of rotation, illuminating an end portion of the disc-shaped object with illumination light, collecting the illumination light reflected from the end portion with an objective lens, capturing an image of the end portion by detecting the reflected light collected by the objective lens, determining a position of the objective lens along the optical axis where the image is brought into focus by using an autofocus optical system, moving the objective lens to the position determined by the autofocus optical system, adding predetermined additional data to data on the image, calculating an amount of eccentricity between the axis of rotation and the center of the disc-shaped object based on positions obtained by one turn of the disc-shaped object, and moving the table based on the amount of eccentricity to correct the amount of eccentricity. According to the configuration described above, the amount of eccentricity can be corrected with accuracy.

The additional data may be a position of the end portion and a position of the objective lens along the optical axis at the time when the image is captured. According to the configuration described above, the amount of eccentricity can be correlated with the position of the end portion.

A plurality of pixels arranged in one direction may image the end portion along the axis of rotation. According to the configuration described above, the amount of eccentricity of the disc-shaped object can be measured with accuracy.

The present invention can provide a measurement apparatus and a measurement method for measuring the amount of eccentricity of a disc-shaped object with accuracy at low cost and further provide a correction method.

The above and other objects, features and advantages of the present invention will become more fully understood from the detailed description given hereinbelow and the accompanying drawings which are given by way of illustration only, and thus are not to be considered as limiting the present invention.

DESCRIPTION OF EMBODIMENTS

A specific configuration of an embodiment of the present invention will be described below with reference to the drawings. The following description shows a preferable embodiment of the present invention, and it is not intended that the scope of the present invention is limited to the following embodiment. In the following description, those having the same reference characters have substantially the same content.

Figure 1:
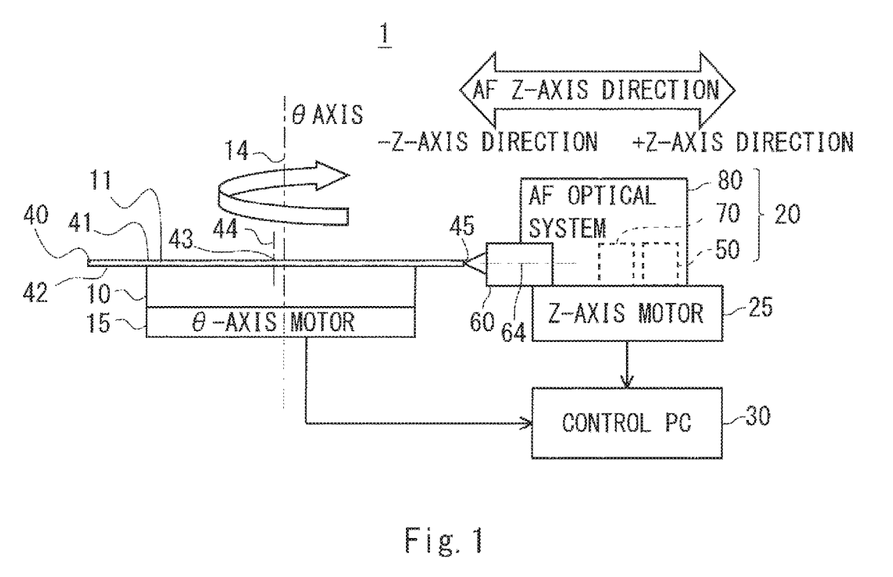
FIG. 1 is a configuration diagram illustrating an overview of a measurement apparatus according to an embodiment.

An overview of the configuration of a measurement apparatus 1 according to the present embodiment will now be described. FIG. 1 is a configuration diagram illustrating an overview of the measurement apparatus according to the embodiment. The measurement apparatus 1 according to the present embodiment includes a table 10, a θ-axis motor 15, an optical system 20, a Z-axis motor 25, and a control unit 30, as shown in FIG. 1. The measurement apparatus 1 measures the amount of eccentricity of a disc-shaped object 40 supported by the table 10 and corrects the amount of eccentricity.

The table 10 has an upper surface 11 and supports the disc-shaped object 40 on the upper surface 11. For example, the disc-shaped object 40 is sucked to be held on the upper surface 11. The table 10 has an axis of rotation 14 extending in the direction perpendicular to the upper surface 11. The table 10 rotates around the axis of rotation 14. Thus, the disc-shaped object 40 supported on the upper surface 11 also rotates around the axis of rotation 14. The direction that intersects the axis of rotation 14 and is perpendicular to the axis of rotation 14 is called a radial direction.

The disc-shaped object 40 is a thin member having the shape of a circular plate and is, for example, a silicon wafer. The disc-shaped object 40 has a front surface 41 and a rear surface 42. The rear surface 42 is in contact with the upper surface 11. The disc-shaped object 40 has a central axis 44, which passes through the center 43 of the disc-shaped object 40 and is perpendicular to the front surface 41 and the rear surface 42. When the disc-shaped object 40 is held on the table 10, the center 43 of the disc-shaped object 40 positionally deviates from the axis of rotation 14 of the table 10 in some cases. The deviation of the center 43 from the axis of rotation 14 is called eccentricity. For example, the amount of eccentricity between the axis of rotation 14 and the center 43 is 100 μm.

The θ-axis motor 15 (first driving unit) rotates the table 10 around the axis of rotation 14. The θ-axis motor 15 is provided, for example, in a position below the table 10. The drive operation of the θ-axis motor 15 is controlled by a control signal from the control unit 30. The θ-axis motor 15 outputs information on the rotation thereof measured, for example, with an encoder to the control unit 30.

The optical system 20 includes a light source 50, an objective lens 60, an imaging unit 70, and an autofocus optical system 80. The optical system 20 further includes a plurality of lenses and half-silvered mirrors and other optical members.

The light source 50 produces illumination light with which an end portion 45 of the disc-shaped object 40 is illuminated. The light source 50 is, for example, a xenon lamp. The light source 50 is not limited to a xenon lamp. The objective lens 60 collects the illumination light reflected from the end portion 45. The optical axis 64 of the objective lens 60 extends along the radial direction perpendicular to the axis of rotation 14 of the table 10. Among directions parallel to the radial direction, the direction that roughly coincides with the optical axis 64 of the objective lens 60 is called a Z-axis direction. The Z-axis direction is also called a focusing direction. Out of the opposite directions that form the Z-axis direction, the direction from the axis of rotation 14 toward the objective lens 60 is called a +Z-axis direction, and the other direction is called a −Z-axis direction.

The Z-axis motor 25 (second driving unit) is attached to the objective lens 60. The Z-axis motor 25 moves the objective lens 60 along the optical axis 64, that is, in the Z-axis direction. The drive operation of the Z-axis motor 25 is controlled by a control signal from the control unit 30. The Z-axis motor 25 outputs information representing the position of the objective lens 60 along the optical axis 64 and measured, for example, with an encoder to the control unit 30.

The imaging unit 70 detects the reflected light collected by the objective lens 60 to capture an image of the end portion 45 of the disc-shaped object 40. The imaging unit 70 is, for example, an image sensor in an imaging camera. The imaging unit 70 outputs the captured image of the end portion 45 to the control unit 30.

The autofocus optical system 80 determines a position where the image of the end portion 45 of the disc-shaped object 40 is brought into focus in the imaging unit 70 and which is the position of the objective lens 60 along the optical axis 64. The autofocus optical system 80 outputs information on the determined position of the objective lens 60 to the control unit 30.

The plurality of lenses and half-silvered mirrors and other optical members guide the illumination light produced by the light source 50 to the end portion 45 of the disc-shaped object 40 and guide the light reflected from the end portion 45 and collected by the objective lens 60 to the imaging unit 70.

The control unit 30 controls the drive operation of the θ-axis motor 15 and the Z-axis motor 25. The control unit 30 drives the θ-axis motor 15 to rotate the table 10 at a predetermined revolving speed. The control unit 30 can therefore determine the position of the end portion 45 of the disc-shaped object 40 at the time when an image of the end portion 45 is captured. Further, the control unit 30 receives information on the position of the objective lens 60 from the autofocus optical system 80. The control unit 30 then drives the Z-axis motor 25 to move the objective lens 60 to the position determined by the autofocus optical system 80.

The disc-shaped object 40 also rotates as the table 10 rotates. In a case where the center 43 of the disc-shaped object 40 deviates from the axis of rotation 14 of the table 10, the Z-axis position of the end portion 45 changes as the disc-shaped object 40 rotates. The autofocus optical system 80 senses the change in the Z-axis position of the end portion 45 on the basis of a shift in the position where the image of the end portion 45 is brought into focus, radiation of auxiliary light, or any other factor. The autofocus optical system 80 then determines a position of the objective lens 60 where the image of the end portion 45 is brought into focus and outputs information on the position to the control unit 30. The control unit 30 moves the position of the objective lens 60 on the basis of the position information received from the autofocus optical system 80. When the disc-shaped object 40 keeps rotating, the Z-axis position of the end portion 45 changes. The autofocus optical system 80 outputs the position of the objective lens 60 to the control unit 30 in such a way that the objective lens 60 follows the change. The control unit 30 causes the objective lens 60 to follow the position received from the autofocus optical system 80. The control unit 30 thus performs feedback control in terms of the position of the objective lens 60.

The control unit 30 adds predetermined additional data to data on the image received from the imaging unit 70. The additional data is formed of, for example, the position of the end portion 45 of the disc-shaped object 40 expressed in the form of the angle of rotation and the position of the objective lens 60 along the optical axis 64 at the time when the image is captured. The additional data is not limited to the data described above. The control unit 30 is, for example, a PC (personal computer).

Figure 2:
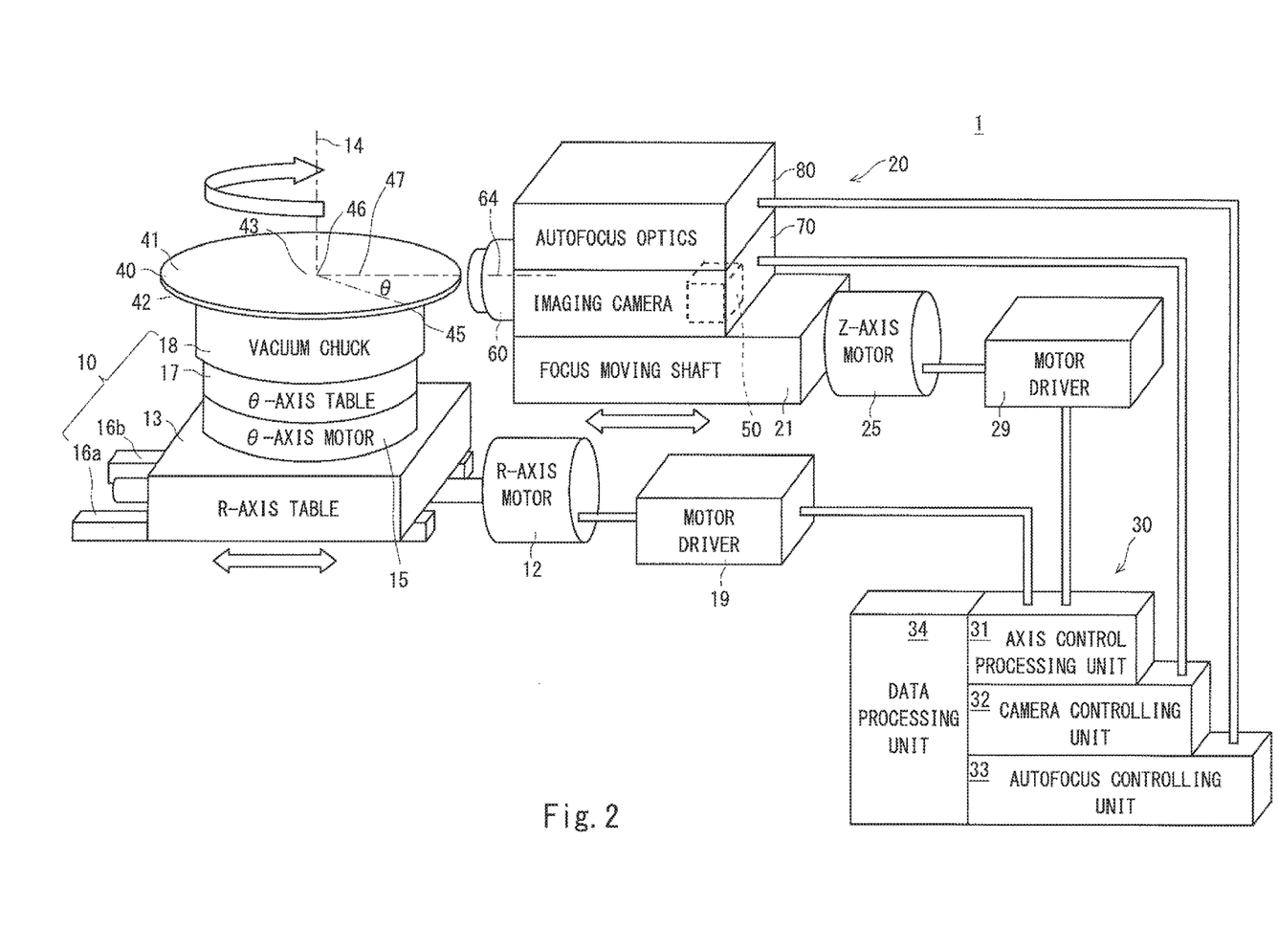
FIG. 2 is a configuration diagram illustrating the measurement apparatus according to the embodiment.

The configuration of the measurement apparatus according to the embodiment will next be described in detail. FIG. 2 is a configuration diagram illustrating the measurement apparatus according to the embodiment. The table 10 includes an R-axis table 13, guides 16a and 16b, a θ-axis table 17, and a vacuum chuck 18, as shown in FIG. 2. The control unit 30 includes an axis control processing unit 31, a camera controlling unit 32, an autofocus controlling unit 33, and a data processing unit 34.

The R-axis table 13 is provided on the guides 16a and 16b. The guides 16a and 16b are fixed, for example, onto a stage and extend in the same direction as the direction along the optical axis 64 of the objective lens 60, that is, the Z-axis direction. The R-axis table 13 can move the disc-shaped object 40 supported on the table 10 along the Z-axis direction by moving along the guides 16a and 16b. The R-axis table 13 thus serves as movement means for moving the table 10. The R-axis table 13 does not necessarily move in the Z-axis direction.

The R-axis table 13 moves when driven by an R-axis motor 12. The drive operation of the R-axis motor 12 is controlled by the axis control processing unit 31 of the control unit 30 via a motor driver 19. For example, the start of movement of the R-axis table 13, the stop of the movement thereof, and the change of the moving speed thereof are performed by the control of the R-axis motor 12 performed by the control unit 30 via the motor driver 19. The R-axis motor 12 outputs information representing the position of the table 10 and measured, for example, with an encoder to the control unit 30.

The θ-axis table 17 is provided on the R-axis table 13. The θ-axis table 17 is a rotating member of the table 10 and rotates around the axis of rotation 14. The θ-axis table 17 rotates when driven by the θ-axis motor 15.

The vacuum chuck 18 is provided on the θ-axis table 17. The vacuum chuck 18 sucks the disc-shaped object 40 placed on the upper surface 11 of the table 10 to support the disc-shaped object 40 on the table.

The θ-axis motor 15 rotates the θ-axis table 17. The drive operation of the θ-axis motor 15 is controlled by the axis control processing unit 31 of the control unit 30 via the motor driver 19. For example, the start of rotation of the θ-axis table 17, the stop of the rotation thereof, and the change of the revolving speed thereof are performed by the control of the θ-axis motor 15 performed by the control unit 30 via the motor driver 19.

The disc-shaped object 40 is supported by the vacuum chuck 18 and on the upper surface 11 of the table 10. The rear surface 42 of the disc-shaped object 40 is sucked by the vacuum chuck 18. The intersection point of the front surface 41 of the disc-shaped object 40 and the axis of rotation 14 is called the center of rotation 46. In the case where the eccentricity is present, the center 43 deviates from the center of rotation 46.

A straight line extending from the center of rotation 46 in an arbitrary direction on the front surface 41 of the disc-shaped object 40 is called a reference line 47. The position of an arbitrary part of the end portion 45 of the disc-shaped object 40 is defined by the angle of rotation θ between the straight line that connects the part of the end portion 45 to the center of rotation 46 and the reference line 47. The end portion 45 of the disc-shaped object 40 can therefore be correlated with the angle of rotation θ, which ranges from 0° to 360° along the entire circumference of the end portion 45.

The position of the end portion 45 expressed in the angle of rotation and corresponding to the reference line 47 is 0°. The position of the end portion 45 expressed in the angle of rotation and corresponding to the straight line rotated from the reference line 47 by 30° is 30°. Assume that the end portion 45 in the position expressed in the angle of rotation of 0° corresponding to the reference line 47 is imaged at the time of the start of the measurement. In this case, the position of the imaged end portion 45 expressed in the angle of rotation θ increases from 0° as the table 10 rotates. A state in which the position of the imaged end portion 45 expressed in the angle of rotation has reached 360° is a state in which the disc-shaped object 40 has made one turn.

The axis control processing unit 31 acquires information on the position expressed in the angle of rotation at the time when an image of the end portion 45 is captured from the information representing the rotation of the θ-axis table 17 and measured by the encoder and transfers the position information to the data processing unit 34. The data processing unit 34 saves the received position information as the additional data.

Bevel surfaces may be formed on the end portion 45 of the disc-shaped object 40. The imaging unit 70 may image the end portion 45 including the bevel surfaces or may image end surface between the bevel surfaces.

A focus moving shaft 21 is attached to the optical system 20. The focus moving shaft 21 moves the objective lens 60 along the optical axis 64 of the objective lens 60, that is, in the Z-axis direction. The focus moving shaft 21 operates when driven by the Z-axis motor 25. The drive operation of Z-axis motor 25 is controlled by the axis control processing unit 31 of the control unit 30 via a motor driver 29. For example, the start of movement of the focus moving shaft 21, the stop of the movement thereof, and the change of the moving speed thereof are performed by the control of the Z-axis motor 25 performed by the control unit 30 via the motor driver 29.

Figure 3:
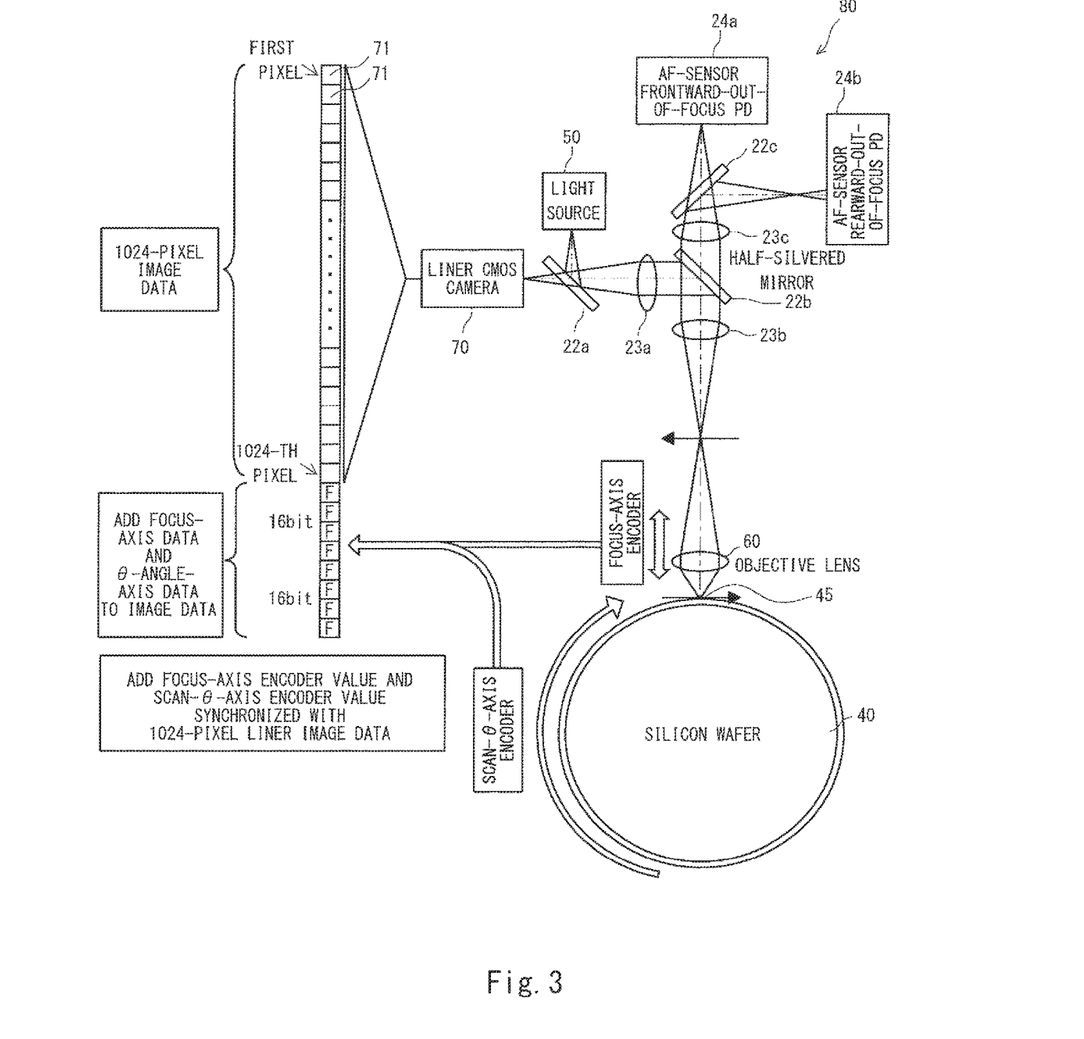
FIG. 3 is a configuration diagram illustrating an optical system of the measurement apparatus according to the embodiment.

FIG. 3 is a configuration diagram illustrating the optical system according to the embodiment. The optical system 20 includes the light source 50, the objective lens 60, the imaging unit 70, the autofocus optical system 80, and the lenses and half-silvered mirrors and other optical members, as shown in FIGS. 2 and 3.

The illumination light produced by the light source 50 is reflected from a half-silvered mirror 22a and passes through a lens 23a. The lens 23a is, for example, an f80 lens. The illumination light having passed through the lens 23a is reflected from a half-silvered mirror 22b and passes through the lens 23b. The lens 23b is, for example, an f50 lens. The light having passed through the lens 23b is collected by the objective lens 60, and the end portion 45 of the disc-shaped object 40 is illuminated with the illumination light. The objective lens 60, for example, is an f20 lens.

On the other hand, the light reflected from the end portion 45 of the disc-shaped object 40 is collected by the objective lens 60. The reflected light collected by the objective lens 60 then passes through the lens 23b and impinges on the half-silvered mirror 22b. Part of the reflected light having impinged on the half-silvered mirror 22b enters the autofocus optical system 80.

The autofocus optical system 80 includes, for example, a lens 23c, a half-silvered mirror 22c, and photodiodes (PDs) 24a and 24b and performs focusing by using a phase difference autofocus method.

In the phase difference autofocus method, for example, the reflected light having entered the autofocus optical system 80 through the lens 23c is divided by the half-silvered mirror 22c into two light fluxes, which are guided to the photodiodes 24a and 24b. Two images formed on the photodiodes 24a and 24b are used to determine the direction and amount required for the focusing. The amount of movement of the objective lens 60 in the +Z-axis direction or −Z-axis direction are thus determined. The autofocus optical system 80 does not necessarily rely on the phase difference autofocus method and may instead rely on a contrast method, an auxiliary beam method, or a confocal method.

The autofocus optical system 80 thus determines a position of the objective lens 60 where an image of the end portion 45 is brought into focus in the imaging unit 70. The autofocus optical system 80 then outputs the determined position of the objective lens 60 to the autofocus controlling unit 33 of the control unit 30. The autofocus controlling unit 33 transfers the information on the position of the objective lens 60 received from the autofocus optical system 80 to the axis control processing unit 31. The axis control processing unit 31 moves the position of the objective lens 60 on the basis of the received position information. The Z-axis position of the end portion 45 changes as the disc-shaped object 40 rotates. The control unit 30 moves the position of the objective lens 60 in such a way that the objective lens 60 follows the change. The control unit 30 thus performs the feedback control.

The autofocus controlling unit 33 transfers the information on the position of the objective lens 60 received from the autofocus optical system 80 to the data processing unit 34. The data processing unit 34 saves the received information on the position of the objective lens 60 as the additional data.

Part of the reflected light having impinged on the half-silvered mirror 22b is reflected from the half-silvered mirror 22b. The reflected light then passes through the lens 23a and impinges on the half-silvered mirror 22a. Part of the reflected light having impinged on the half-silvered mirror 22a passes through the half-silvered mirror 22a and enters the imaging unit 70. The imaging unit 70 detects the incident reflected light to acquire the image of the end portion 45.

The imaging unit 70 is, for example, an image sensor in the imaging camera. For example, the imaging unit 70 has a plurality of pixels 71 linearly arranged in one direction. For example, 1024 pixels 71 are linearly arranged. For example, the pixels 71 formed of a 0-th pixel to a 1023-th pixel are arranged. The plurality of pixels 71 arranged in one direction image the end portion 45 of the disc-shaped object 40 along the axis of rotation 14. For example, the 0-th pixel 71 images a point on the end portion 45 and in an area extending along the axis of rotation 14, the point closest to the rear surface 42 in the area, and the 1023-th pixel 71 images the point closest to the front surface 41 in the area. That is, a pixel 71 having a smaller number images a point closer to the rear surface 42, and a pixel 71 having a greater number images a point closer to the front surface 41. Instead, a pixel 71 having a smaller number may image a point closer to the front surface 41. The imaging unit 70 thus acquires an image of an area of the end portion 45 of the disc-shaped object 40, the area extending along the axis of rotation 14. The imaging unit 70 outputs information on the acquired image to the camera controlling unit 32 of the control unit 30.

The camera controlling unit 32 receives data on the image captured by the imaging unit 70. The camera controlling unit 32 transfers the received image data to the data processing unit 34. The camera controlling unit 32 controls the start and stop of the imaging performed by the imaging unit 70 and other actions associated with the imaging.

The data processing unit 34 adds the additional data to the image data. The image data is data corresponding to the 1024 pixels 71. Data from each of the pixels 71 is, for example, 16-bit data. The data processing unit 34 adds additional data corresponding to several pixels to the image data. For example, the data processing unit 34 adds, as the additional data, the position of the end portion 45 expressed in the form of the angle of rotation (data correlated with angle θ) and the position of the objective lens 60 (data on position on focus axis) at the time when the image of the end portion 45 is captured. The data processing unit 34 adds the additional data in synchronization with the imaging operation. The additional data is not limited to the position of the end portion 45 expressed in the form of the angle of rotation and the position of the objective lens 60 at the time when the image of the end portion 45 is captured.

A measurement method will next be described as the action of the measurement apparatus 1 according to the embodiment.

A silicon wafer is placed as the disc-shaped object 40, which is a target to be measured, on the table 10, as shown in FIGS. 1 to 3. The vacuum chuck 18 is then used to suck the disc-shaped object 40 and placed on the table 10. The disc-shaped object 40 is thus supported on the table 10 having the axis of rotation 14. The disc-shaped object 40 is not limited to a silicon wafer.

The axis control processing unit 31 of the control unit 30 is then activated and controlled to output a control signal that drives the θ-axis motor 15 to the motor driver 19. The motor driver 19 then drives the θ-axis motor 15 to rotate the table 10 around the axis of rotation 14 at a predetermined revolving speed.

On the basis of information on the rotation of the table 10, information on the position of the end portion 45 expressed in the form of the angle of rotation at the time when an image of the end portion 45 is captured is acquired. For example, the axis control processing unit 31 acquires information on the position of the end portion 45 expressed in the form of the angle of rotation at the time when an image of the end portion 45 is captured is acquired. The acquired position information is transferred to the data processing unit 34, which saves the position information as the additional data.

When the θ-axis table 17 rotates, the disc-shaped object 40 supported by the θ-axis table 17 also rotates. At this point, the center 43 of the disc-shaped object 40 deviates from the axis of rotation 14 of the θ-axis table 17 in some cases, and the deviation is called the amount of eccentricity, as described above.

The optical members that form the optical system 20 are then disposed in predetermined positions. That is, the end portion 45 of the disc-shaped object 40 is illuminated with the illumination light produced by the light source 50, and the illumination light reflected from the end portion 45 is collected by the objective lens 60. The optical axis 64 of the objective lens 60 is aligned with the radial direction perpendicular to the axis of rotation 14 of the table 10. The thus aligned direction along the optical axis 64 is called the Z-axis direction, and the objective lens 60 is caused to face the end portion 45 of the disc-shaped object 40.

The light source 50 is then activated to produce the illumination light, and the end portion 45 of the disc-shaped object 40 is illuminated with the illumination light. The illumination light reflected from the end portion 45 is then collected by the objective lens 60.

Part of the reflected light collected by the objective lens 60 is then caused to reach the autofocus optical system 80. The autofocusing that brings the image of the end portion 45 into focus then determines a position of the objective lens 60 where the image of the end portion 45 is brought into focus in the imaging unit 70. The objective lens 60 is then moved along the optical axis 64, that is, in the Z-axis direction to the determined position of the objective lens 60.

Information on the position of the objective lens 60 is acquired. For example, the autofocus controlling unit 33 acquires information on the position of the objective lens 60 where the image of the end portion 45 is brought into focus in the imaging unit 70. The acquired position information is transferred to the data processing unit 34 and saved as the additional data.

On the other hand, part of the reflected light collected by the objective lens 60 is caused to reach the imaging unit 70. The imaging unit 70 then detects the reflected light collected by the objective lens 60 to capture the image of the end portion 45.

Data on the image captured by the imaging unit 70 is then outputted to the control unit 30. The control unit 30 then adds predetermined additional data to the image data received from the imaging unit 70. For example, the additional data is formed of the position of the end portion 45 expressed in the form of the angle of rotation and the position of the objective lens 60 along the optical axis 64 at the time when the image of the end portion 45 is captured.

Figure 4:
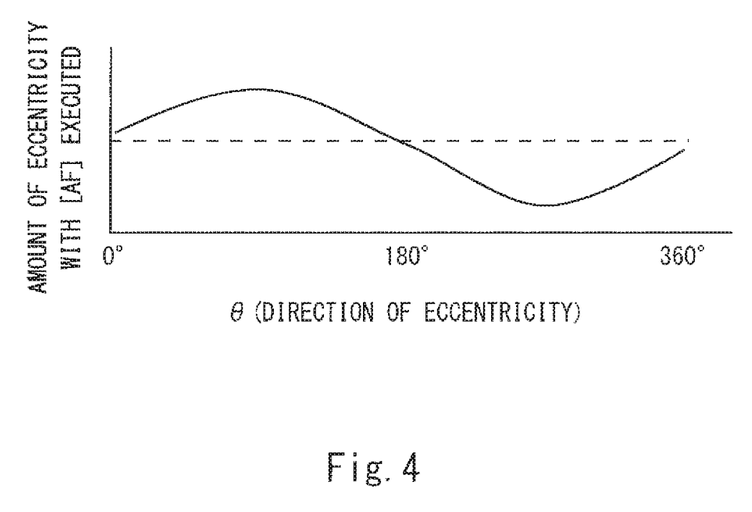
FIG. 4 is a graph illustrating the amount of eccentricity measured by using a measurement method according to the embodiment with the horizontal axis representing the position of an end portion expressed in the form of the angle of rotation and the vertical axis representing the amount of eccentricity represented by the on-optical-axis position of an objective lens.

FIG. 4 is a graph illustrating the amount of eccentricity measured by using the measurement method according to the embodiment. In FIG. 4, the horizontal axis represents the position of the end portion expressed in the form of the angle of rotation (position corresponding to angle θ), and the vertical axis represents the amount of eccentricity represented by the on-optical-axis position of the objective lens. The dotted line represents an ideal case where no eccentricity is present.

The position of the objective lens 60 changes along the optical axis 64 in accordance with the position of the end portion 45 expressed in the form of the angle of rotation, as shown in FIG. 4. For example, the positions of the objective lens 60 at the time when parts of the end portion 45 that correspond to angles of rotation of 0° and 180° are imaged are each the ideal position, where the amount of eccentricity is small, as shown in FIG. 4. On the other hand, the position of the objective lens 60 at the time when part of the end portion 45 that corresponds to an angle of rotation of 90° is imaged greatly shifts in the +Z-axis direction. Conversely, the position of the objective lens 60 at the time when part of the end portion 45 that corresponds to an angle of rotation of 270° is imaged greatly shifts in the −Z-axis direction.

The control unit 30 calculates the amount of eccentricity between the axis of rotation 14 and the center of the disc-shaped object 40 based on the positions of the objective lens 60 along the optical axis 64 that are obtained by one turn of the disc-shaped object 40. For example, the control unit 30 divides the sum of the maximum and minimum of the position of the objective lens 60 by 2 as the amount of eccentricity between the axis of rotation 14 and the center 43. The measurement apparatus 1 thus measures the amount of eccentricity.

A correction method in which the measurement apparatus 1 corrects the amount of eccentricity will next be described. The configuration of an apparatus to be used and the method for measuring the amount of eccentricity are the same as the configuration of the measurement apparatus 1 and the measurement method described above and will not therefore be described.

The control unit 30 corrects the amount of eccentricity by moving the table 10 on the basis of the amount of eccentricity measured by the measurement apparatus 1. Specifically, the axis control processing unit 31 of the control unit 30 moves the R-axis table 13 along the optical axis 64 in such a way that the amount of eccentricity in the position of part of the end portion 45 that corresponds to an angle of rotation θ saved in the data processing unit 34 is eliminated, that is, the amount of movement equal to but having the opposite sign of the amount of eccentricity in the position of the part of the end portion 45 that corresponds to the angle of rotation θ is achieved. For example, when part of the end portion 45 that corresponds to the angle of rotation of 90° reaches the imaging position, the R-axis table 13 is moved in the −Z-axis direction. When part of the end portion 45 that corresponds to the angle of rotation of 270° reaches the imaging position, the R-axis table 13 is moved in the +Z-axis direction. The drive operation of the R-axis table 13 is controlled by the control unit 30 via the motor driver 19. In the feedback control, additional data created in consideration of the amounts of delay in the response of drive operation of the R-axis table and drive operation of the objective lens 60 in the Z-axis direction can be used.

Figure 5:
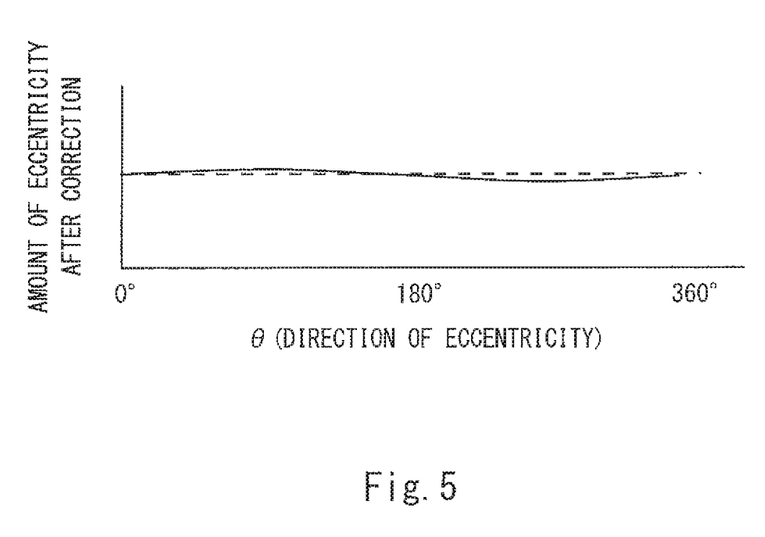
FIG. 5 is a graph illustrating the amount of eccentricity corrected by using a correction method according to the embodiment with the horizontal axis representing the position of the end portion expressed in the form of the angle of rotation and the vertical axis representing the amount of eccentricity represented by the on-optical-axis position of the objective lens.

FIG. 5 is a graph illustrating the amount of eccentricity corrected by using the correction method according to the embodiment. In FIG. 5, the horizontal axis represents the position of the end portion expressed in the form of the angle of rotation, and the vertical axis represents the amount of eccentricity represented by the on-optical-axis position of the objective lens. Moving the table 10 in the Z-axis direction in such a way that the amount of eccentricity is eliminated allows suppression of the amount of eccentricity, as shown in FIG. 5.

An effect provided by the present embodiment will next be described. The measurement apparatus 1 calculates the amount of eccentricity of the disc-shaped object 40 on the basis of the position of the objective lens 60 determined by autofocusing. The amount of eccentricity of the disc-shaped object can thus be measured with accuracy at low cost.

Further, the position of the end portion 45 expressed in the form of the angle of rotation and the position of the objective lens 60 along the optical axis 64 at the time when an image of the end portion 45 is captured are added to data on the image. The position of the end portion 45 expressed in the form of the angle of rotation and the on-optical-axis position of the objective lens 60 at the time when the image is captured can thus be correlated with each other. Since the addition of the additional data is performed simultaneously with the imaging, the period required for acquisition of the data can be shortened.

Further, the imaging unit 70 includes the plurality of pixels 71 arranged in one direction and images the end portion 45 along the axis of rotation 14. The end portion 45 can therefore be imaged in detail, whereby the accuracy of the amount of eccentricity can be further improved.

The additional data can also contain data other than the position of the end portion 45 and the position of the objective lens 60, whereby a variety of types of data can be added to image data.

In the measurement apparatus 1, the end portion 45 is imaged, for example, in the form of an 8×-maginified image by using the lenses and other components of the optical system 20. Further, in the imaging unit 70, 1024 pixels each having a width of 14 μm are arranged in a single row. The field of view therefore has a size of 1.792 mm derived by 14 μm×1024 pixels÷8. On the other hand, the length of the circumference of a 300-mm wafer is 942.47 mm. Therefore, in a case where the wafer is imaged along the entire circumference thereof, 525 images are captured. On the other hand, since the imaging unit 70 is operated at 60 kHz, the images of the end portion 45 that correspond to one turn can be acquired by causing the wafer to make one turn in 8.96 seconds derived by 525 images×1024 pixels÷60. That is, the revolving speed can be set at 0.11 rps. As described above, causing the disc-shaped object 40 to make one turn in 8.96 seconds allows generation of images of the end portion 45 of the disc-shaped object 40 and the position of the end portion 45 and the position of the objective lens 60 along the optical axis 64 at the time when the images are captured. The period required for the measurement of the amount of eccentricity can therefore be shortened.

Since the amount of eccentricity can be measured without acquisition of an image of any portion of the front surface 41 of the disc-shaped object 40, the period required for the imaging can be shortened, and the capacity of a memory that saves images can be reduced.

Further, since the same measurement apparatus 1 can also be used for the correction of the amount of eccentricity, the period required for the correction of the amount of eccentricity of the disc-shaped object 40 can be shortened. Moreover, the measurement apparatus 1 can be used to scan the disc-shaped object 40 having a reduced amount of eccentricity.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A measurement apparatus comprising:
   a table that has an axis of rotation and supports a disc-shaped object;
   a first driving unit that rotates the table around the axis of rotation;
   a light source that produces illumination light with which an end portion of the disc-shaped object is illuminated;
   an objective lens that collects the illumination light reflected from the end portion;
   a second driving unit that moves the objective lens along an optical axis of the objective lens;
   an imaging unit that captures an image of the end portion by detecting the reflected light collected by the objective lens;
   an autofocus optical system that determines a position of the objective lens along the optical axis where the image is brought into focus in the imaging unit; and
   a control unit that controls the first driving unit and the second driving unit,
   wherein the control unit moves the objective lens to the position determined by the autofocus optical system and adds predetermined additional data to data on the image.

2. The measurement apparatus according to claim 1, wherein the additional data is of a position of the end portion and of a position of the objective lens along the optical axis at the time when the image is captured.

3. The measurement apparatus according to claim 1, wherein the imaging unit includes a plurality of pixels arranged in one direction, and the plurality of pixels image the end portion along the axis of rotation.

4. The measurement apparatus according to claim 1, wherein the control unit calculates an amount of eccentricity between the axis of rotation and the center of the disc-shaped object based on positions of the objective lens along the optical axis that are obtained by one turn of the disc-shaped object.

5. The measurement apparatus according to claim 4, further comprising a third driving unit that moves the table, wherein the control unit moves the table based on the amount of eccentricity.

6. A measurement method comprising:
placing a disc-shaped object on a table having an axis of rotation;
rotating the table around the axis of rotation;
illuminating an end portion of the disc-shaped object with illumination light;
collecting the illumination light reflected from the end portion with an objective lens;
capturing an image of the end portion by detecting the reflected light collected by the objective lens;
determining a position of the objective lens where the image is brought into focus and which is a position along an optical axis of the objective lens by using an autofocus optical system;
moving the objective lens to the position determined by the autofocus optical system; and
adding predetermined additional data to data on the image.

7. The measurement method according to claim 6, wherein the additional data is of a position of the end portion and of a position of the objective lens along the optical axis at the time when the image is captured.

8. The measurement method according to claim 6, wherein a plurality of pixels arranged in one direction image the end portion along the axis of rotation.

9. The measurement method according to claim 6, wherein an amount of eccentricity between the axis of rotation and the center of the disc-shaped object is calculated based on positions of the objective lens along the optical axis that are obtained by one turn of the disc-shaped object.

10. A correction method comprising:
placing a disc-shaped object on a table having an axis of rotation;
rotating the table around the axis of rotation;
illuminating an end portion of the disc-shaped object with illumination light;
collecting the illumination light reflected from the end portion with an objective lens;
capturing an image of the end portion by detecting the reflected light collected by the objective lens;
determining a position of the objective lens where the image is brought into focus and which is a position along an optical axis of the objective lens by using an autofocus optical system;
moving the objective lens to the position determined by the autofocus optical system;
adding predetermined additional data to data on the image;
calculating an amount of eccentricity between the axis of rotation and the center of the disc-shaped object based on positions obtained by one turn of the disc-shaped object; and
moving the table based on the amount of eccentricity to correct the amount of eccentricity.

11. The correction method according to claim 10, wherein the additional data is of a position of the end portion and of a position of the objective lens along the optical axis at the time when the image is captured.

12. The correction method according to claim 10, wherein a plurality of pixels arranged in one direction image the end portion along the axis of rotation.

\* \* \* \* \*